US005972861A

United States Patent [19]

Rolfes

[11] Patent Number: 5,972,861

[45] Date of Patent: Oct. 26, 1999

[54] LAUNDRY DETERGENT BAR CONTAINING SOAP, AND METHYLESTER SULFONATE SURFACTANTS

[75] Inventor: Thomas R. Rolfes, Wyoming, Ohio

[73] Assignee: Corporacion Cressida, Tegucigalpa, Honduras

[21] Appl. No.: 08/827,119

[22] Filed: Mar. 27, 1997

[51] Int. Cl.[6] .......... A61K 7/50

[52] U.S. Cl. .......... 510/152; 510/155; 510/156

[58] Field of Search .......... 510/351, 352, 510/357, 298, 383, 426, 427, 428, 429, 422, 424, 141, 152, 156; 134/40; 560/147

[56] References Cited

U.S. PATENT DOCUMENTS

| | | | |
|---|---|---|---|
| 3,632,517 | 1/1972 | Stlirton et al. | 252/109 |
| 4,194,986 | 3/1980 | Tournier et al. | 252/102 |
| 4,416,809 | 11/1983 | Magari et al. | 252/557 |
| 5,262,079 | 11/1993 | Kacher et al. | 252/112 |
| 5,616,781 | 4/1997 | Sajic et al. | 510/221 |
| 5,637,758 | 6/1997 | Sajic et al. | 560/147 |

FOREIGN PATENT DOCUMENTS

| | | |
|---|---|---|
| 42 42 185 A1 | 6/1994 | Germany . |
| 1014058 | 12/1965 | United Kingdom . |
| 2 179 055 | 2/1987 | United Kingdom . |
| WO 96/35772 | 11/1996 | WIPO . |

OTHER PUBLICATIONS

Abstract of XP002071515, Patent Number CN 1 089 987 A, "Paste Detergent Containing Fatty Acid Methylester Sodium Sulphonate," *Derwent Publications Ltd.,* London, GB, Section Ch, Week 9713, Jul. 27, 1994.

*Primary Examiner*—Necholus Ogden
*Attorney, Agent, or Firm*—Fish & Richardson P.C.,P.A.

[57] ABSTRACT

A hand laundry detergent and composition includes a surfactant mixture containing a base soap and one or more fatty acid methyl ester sulfonates (MES) having the formula:

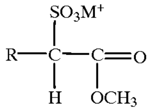

wherein R is a fatty alkyl chain having 6–20 carbon atoms, M+ is a monovalent or divalent salt. A method for cleaning soiled fabrics and/or laundry which includes treating the laundry and/or fabrics with this detergent composition is also provided.

21 Claims, No Drawings

LAUNDRY DETERGENT BAR CONTAINING SOAP, AND METHYLESTER SULFONATE SURFACTANTS

BACKGROUND OF THE INVENTION

The present invention relates to detergent compositions, and in particular, hand laundry compositions containing methylester sulfonate surfactants. In one preferred embodiment, the present invention relates to laundry bar compositions which possess excellent cleaning, whitening/anti-redeposition, foaming properties, and are mild to the skin.

Detergent compositions are well recognized in the art and can vary greatly in composition depending on end use. However, such compositions typically include anionic sulfate or sulfonate surfactants, and in particular linear alkyl benzene sulfonates (LAS).

Hand laundry detergent compositions, such as laundry soap bars, are used for hand laundering clothes at ambient temperatures. It has been found that soap employed for laundry purposes should be a little stronger than that soap used for cosmetic and/or hand use in order to effectively remove soils from fabrics. Moreover, hand laundering compositions are required to have a relatively high degree of foaming. This is in contrast to machine wash compositions where little or no foam is desired.

Hand laundering compositions are also very cost sensitive. In view of the fact that they are typically employed in emerging world economies, cost becomes a significant consideration in formulating these detergent compositions. Most producers of such compositions typically include soap at a 60% level since it is a relatively low cost surfactant. Thus, hand laundering compositions need to provide a suitable combination of performance, foam and cost.

The art has also looked to the improvement of these compositions through the inclusion of additional surfactants such as alkylbenzone sulfonates and in particular, LAS. In making improvements in laundry soap formulations, e.g., through the use of LAS or other alkyl benzene sulfonates, the surfactants are chosen for both their performance and their cost.

In this regard, methyl ester sulfonates have been employed in certain detergent compositions. However, methyl ester sulfonates have normally been employed only in combination with another primary surfactant such as LAS, e.g. in detergent granules and certain liquid detergent products. They have not been found in hand laundry compositions.

Perhaps most significantly, MES as the sole surfactant has failed to meet the cost-foam-performance requirements in soft water environments, and from the performance side, compositions containing both LAS & MES have not provided significant improvements in soft water environments. Thus, MES certainly has not been viewed as a replacement for LAS.

Since one typically expects harder water will lead to poorer foaming and performance, particularly with low cost laundry soap bars, the art has not contemplated the use of MES in detergent compositions for such environments.

In other words, while MES has been employed as an additive in combination with, e.g., LAS, it has not found use as a replacement for LAS. In fact, its relatively poor performance in combination with LAS, has led the art in other directions.

SUMMARY OF THE INVENTION

The present invention is based on the surprising discovery that laundry detergent compositions, and in particular hand laundry compositions, containing a surfactant mixture, e.g., conventional soap and MES, are capable of providing improved foaming and cleaning performance as compared to traditional laundry compositions relying on alkyl benzene sulfonates and soap. In fact, the detergent compositions of the present invention can provide these advantages in the absence of traditional surfactants such as LAS, thus, MES can be used as an effective replacement for such surfactants.

In addition to the performance benefits that the detergent compositions can provide, the compositions according to the present invention can be milder to the hands than those formulas using traditional surfactants, e.g., alkyl benzene sulfonates, as the principal anionic surfactant.

In one aspect, the present invention relates to detergent compositions comprising a surfactant mixture containing effective amounts of:

(a) a base soap, and (b) one or more fatty acid methyl ester sulfonates (MES) having the formula:

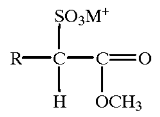

wherein R is a alkyl chain having 6–20 carbon atoms, preferably 12–18 carbon atoms, M+ is a monovalent or divalent salt, to provide a hand laundry detergent composition.

In another aspect, the present invention relates to a method for cleaning soiled fabrics and/or laundry which comprises treating the laundry/fabrics with a detergent composition of the present invention.

DETAILED DESCRIPTION OF THE PREFERRED EMBODIMENTS

The detergent composition according to the present invention includes a surfactant mixture comprising a base soap and at least one fatty acid methyl ester sulfonate (MES). In one preferred embodiment, the composition is at least substantially free, and preferably totally free, of any other anionic surfactants, such as linear alkyl sulfonates (LAS). By "substantially free", it is meant that LAS is present in an amount less than that needed if LAS were the primary surfactant, such an amount is less than 5% preferably less than 2% by weight.

The amount of this surfactant mixture present in the detergent composition is that amount which allows effective use of the composition in hand laundry applications. In particular, the amounts provide a combination of performance and foaming suitable for hand laundering of fabrics. This amount is typically from about 5% to about 85% by weight, preferably from about 40% to 80% by weight, most preferably from about 50% to 75% by weight of the surfactant mixture.

As discussed above, the surfactant mixture employed in the present invention includes at least two surfactants, a soap and a fatty acid methyl ester sulfonate (MES). A first component of the surfactant mixture of the present invention is preferably a base soap. Any art-recognized soap for use in laundry, and in particular, hand laundry application can be employed as the "base soap" of the present invention. For example, suitable soaps include combinations of natural fatty acids derived from tallow and/or coconut, palm, palm kernel or other oil bearing seeds with chainlengths in the range $C_8$ to $C_{22}$. Such soaps are common in the art, and are not unique in character to this invention. These soaps may, optionally, be neutralized in a manner recognized in the art, e.g., with sodium ions or the like.

Moreover, suitable base soap preferably contain 15–21%, more preferably 18% by weight, of water.

The base soap is present in an amount of about 5–95% by weight of the surfactant mixture, preferably 50–90%, and more preferably 80–86%.

A second component of the surfactant mixture is at least one fatty acid methyl ester sulfonate (MES).

The fatty acid methyl ester sulfonates suitable for one in the present invention include any of those methyl ethyl sulfonates recognized within the art with methyl ethyl sulfonates having an alkyl chain length of 12–18 carbon atoms being preferred.

In this regard, alkyl chainlengths less than 12 may provide inferior cleaning performance while alkyl chainlengths greater than 18 carbon atoms would likely be poorly soluble in most detergent compositions for consumer use at ambient temperatures.

The methyl ester sulfonates of the present invention can be produced from natural materials, e.g., various oil seed extracted oils, palm, palm kernel, coconut, cotton, soy and the like, or synthetic materials, e.g., synthetic fatty alcohols.

The MES are preferably present in an amount of about 5–95 % of the surfactant mixture, more preferably 5–25% and still more preferably 10–15% by weight.

Specific examples of suitable fatty acid methyl ester sulfonates for use in the present invention include from about 3% to about 25% by weight of the detergent composition mixture, more preferably from about 10% to about 18%, still more preferably from about 8% to about 15% of a mixture of $C_{12}$–$C_{14}$ MES and $C_{16}$–$C_{18}$ MES in ratios from about 1:100 to 1:4 of the $C_{12}$–$C_{14}$:$C_{16}$–$C_{18}$ chainlengths. Although not required, MES is normally sodium neutralized, but may be neutralized with other traditional salts such as potassium and the like. Moreover, the MES may also be neutralized, in whole or in part, by divalent ions, e.g., magnesium.

Methods for making MES are recognized in the art. For example, they can be produced by reacting fatty acid methyl esters with dilute sulfur trioxide gas in a falling film reactor at a mole ratio of about 1.2:1 $SO_3$:feed. The fatty acid methyl ester feedstock has been extensively hydrogenated to minimize the presence of double bonds from the original triglyceride oil feed. Typical iodine values (IV's) for high quality methyl esters intended for sulfonation are less than 1, preferably less than 0.5.

The subsequent sulfonic acid is bleached with, e.g., methanol and hydrogen peroxide, before neutralization to improve the color of the resultant methyl sulfonate and reduce the level of the desalt formation.

By "desalt" it is meant those compounds having the formula:

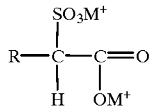

where M+ is a neutralizing agent typically a Na salt.

Because desalts are considered poor surfactants, they are considered a "load" on the detergent system. Accordingly, it is preferred that only a minor amount, if any, of the desalt is present. By "minor amount" it is meant an amount less than that which has a significant adverse effect upon the surfactant system. In particular, it is desired that there is less than about 4% of desalt present within the MES used in the detergent composition according to the present invention.

Preferably, after neutralization, the methyl ester sulfonate is reduced to low moisture (3–30% $H_2O$) by a suitable technique, e.g., in a steam heated, vacuum flash device, under controlled temperature and pressure conditions to assure the quality of the resulting MES. Suitable processing apparatuses are available commercially, available from the Chemithon Company (Seattle, Washington) and Ballestra company (Milan, Italy).

MES, upon drying, go through a 'middle phase' phenomena similar to many surfactants such as alkyl ethoxy sulfates, and, as such, need to be carefully treated to reduce the moisture level sufficiently to be utilized in laundry/soap bars. Moisture, particularly at higher pH's can cause reversion of the MES and formation of the desalt. Accordingly, it is desirable to prevent the presence of excess moisture, e.g., less than about 40% by weight, in combination with high temperatures, e.g., greater than 80° C., and pH's in excess of 10. Suitable treatment teachings are recognized in the art and, as such, will not be discussed here.

The MES utilized in the present invention are nominally at neutral pH. Moreover, when incorporated into the laundry bar, the pH is likely to be about pH 10. The use of a pH significantly above 10, or below about pH 5, are not preferred due to possible hydrolysis of the methyl ester sulfonate. The specific example of a preferred composition includes 1% to 6% $C_{12-14}$ methyl ester sulfonate, 1% to 20% $C_{16-18}$ methyl ester sulfonate, and 50%–70% base soap based on the total weight of the composition.

The compositions of the present invention may, optionally, include minor amounts of additional surfactant materials such as alcohol ethoxy sulfates, alkyl benzene sulfonates, alkyl ethoxylates, alkyl amine oxides, betaines, alkyl mono-, di- or tri- ethanol amides, alkyl polygluocide, glucose amide, and alkyl ethoxy carboxylates. Specific examples of such additives includes alkyl ethoxy (0.1–4) sulfate, alkyl poly glucicide, alkyl dimethyl amine oxide, or an alkyl ethoxylate nonionic where the alkyl group contains from 8 to 14 carbon atoms, and the degree of ethoxylation (C—C═O)x is from 6 to 12.

These surfactants, which are preferably present individual amounts of 0.5 to 5% by weight and cumulatively at levels not greater than 10% by weight of the formulation, can provide certain aesthetic benefits or bar physical properties.

However, it should be clear that, as optional components, the present invention includes those compositions in which any or all of these additional surfactants are specifically excluded therefrom.

Other non-surfactant additive suitable for use in the present invention include those additives found in traditional laundry detergent compositions. Such additives include sequesterants, builders, enzymes, brighteners and the like. The only limitation in the use of such additives is that they do not degrade either the composition or the material it cleans.

The composition of the present invention can be in solid, liquid, paste, granular, agglomerate or bead form with the solid or semi-solid form being preferred. The preferred solid or semi-solid bar can have any shape, e.g., disk, cylinder, sphere, or other extruded shapes and/or stamped, suitable for hand laundry use.

The laundry composition is then made in the desired form, e.g., solid or semi-solid by techniques recognized in the art.

Moreover, the laundry compositions can be used in the same manner as traditional compositions.

In particular, the hand laundry compositions can provide effective cleaning and foaming performance especially in hard water environments. By "hard" it is meant water having generally greater than 15 grains of hardness per gallon, with "soft" being less than about 5 grains per gallon and "medium" hardness being about 5 to about 15 grains per gallon.

The hardness of water varies greatly from locality to locality. However, many commercial water systems around the world, can have a hardness as high as 25 grains per gallon. The compositions of the present invention are capable of providing a significant increase in foaming, as evidenced by the Foam Index, at high hardness levels.

The laundry compositions according to the present invention are capable of not only providing unexpectedly superior laundry cleaning and foaming performance, but mildness to hand as compared with traditional detergent compositions.

EXAMPLES

The following examples illustrate the practice of the present invention, but are not intended to be limiting thereof.

Example 1

A suitable process for making fatty acid methyl ester sulfonates for use in the present invention is as follows: Upon extraction of oil from an oilbearing seed, in this example but not limited, the fruit of oil palm, the resultant oil is refined, bleached and deodorized in typical fashion. The treated oil is then converted to the methyl ester by the addition of methanol in a transesterification reaction using a sodium methylate or other suitable catalyst. The process, which may be either batch or continuous process, results in a mixture of methyl esters, methanol, and glycerine which is subsequently separated by washing and distillation.

At this point, the methyl esters are hydrogenated under moderate pressure in the presence of a catalyst, e.g., a nickel catalyst having a large surface area, to remove unsaturation from the methyl esters. This step further enables the subsequent sulfonation step to produce high quality, good color methyl ester sulfonates.

After hydrogenation, the resulting methyl esters with iodine values (IV's) less than 1, preferably less than 0.5, are distilled to separate the mixture of esters into fractions suitable for use in a detergent composition, and in particular, a laundry bar.

For example, palm oil methyl esters can be fractionated to produce a predominant $C_{16}$–$C_{18}$ methyl ester feed stock, while palm kernel oil methyl esters can be fractionated to produce a more desirable $C_{12}$–$C_{14}$ methyl esters. These may be further fractionated, if desired, to individual chainlengths.

The resultant purified and selected methyl esters become the feedstock for the sulfonation reaction. The methyl ester is fed, e.g., as a thin, falling film, to a reactor in the presence of an air-sulfur trioxide mixture generally at a molar ratio of 1.2 to 1.3 of the stoichiometric amount needed to react with the methyl ester feedstock.

Sulfonation Proceeds in Two Steps:

The first step is a rapid reaction of the methyl ester with two moles of $SO_3$ to form an adduct. This can be accomplished, for example, in a standard falling film sulfonator.

The second step is rearrangement of the adduct to form methyl ester sulfonate. This step also releases the second molecule of $SO_3$ which is then free to further react with another methyl ester molecule. The second reaction is slow and requires an extended digestion time of, e.g., 20 to 40 minutes, and elevated temperature, e.g., on the order of 70° C. to go to completion. This use of elevated temperature can darken the product and, thus, a bleaching step may be performed to lighten the final product to acceptable formulation levels for the desired product.

A preferred bleaching method for production of highest quality methyl ester sulfonate involves the addition of methanol in amounts in excess of about 30–50% of the methyl ester sulfonate acid, along with concentrated hydrogen peroxide, about 50% $H_2O_2$, so as to improve the color of the resultant product while avoiding the risks associated with hypochlorite bleaching. Moreover, the undesirable production of desalt is minimized, as is hydrolysis of the subsequent active material.

The resultant mixture is allowed to digest for an optimum period, and then neutralized, typically with sodium hydroxide. The yield to desalt is reduced with digestion, and reaches a minimum in about 60 minutes. The resulting neutralized methyl ester sulfonated mixture is then stripped of residual methanol and dried in to concentrations 70% active matter or higher to make the MES suitable for incorporation into the bar. An example of a suitable drying apparatus is the TurboTube® Dryer of Chemithon Company.

Example 2

The following compositions show first a standard composition laundry bar, noting only the key components: Base soap, which can be palm, palm kernel, coconut, or tallow soap or combinations thereof, then sodium carbonate as a source of alkalinity, surfactant, which in the case of the standard sample is alkyl benzene sulfonate, and the balance being moisture and minor components such as fragrance, color, etc.

The examples of this table show replacement of the Alkyl Benzene Sulfonate with various levels of Methyl Ester Sulfonate (MES) $C_{16-18}$ chainlength. Foam Index is then determined by way of the Ross/Miles test, which is an art-recognized test. The examples show the impact of hardness on the foam properties compared to the standard indexed at 100 for the initial and final readings (after 15 min). It should be noted that one grain per gallon of hardness corresponds to about 17 ppm hardness.

TABLE 1

| | COMPOSITION (PERCENT BY WEIGHT) | | | |
|---|---|---|---|---|
| | STD | S1 | S2 | S3 |
| COMPOSITIONS | | | | |
| Base Soap (~18% moisture) | 62 | 62 | 62 | 52 |
| Sodium Carbonate | 4 | 4 | 4 | 4 |
| Alkylbenzene Sulfonate | 10 | 5 | 3 | 3 |
| $C_{16}$–$C_{18}$ MES | — | 5 | 8 | 18 |
| Moisture/Misc | 24 | 24 | 23 | 23 |
| FOAM INDEX: Initial/Final | | | | |
| 50 ppm hardness | 100/100 | 97/100 | 97/99 | 97/98 |
| 150 ppm hardness | 100/100 | 92/94 | 91/92 | 89/88 |
| 300 ppm hardness | 100/100 | 227/3000 | 465/7400 | 724/12800 |

Example 3

The following table is included to show the addition of 2 parts of $C_{12-14}$ MES to the compositions, first keeping the total MES content at 10 parts, replacing the alkylbenzene sulfonate, and then the addition of more $C_{16-18}$ MES. This example illustrates the benefit of MES on foaming at hard water vs. the standard, or tailoring the formula to whatever hardness is desired.

TABLE 2

| | STD | 4XA | 5XA | 6XA |
|---|---|---|---|---|
| COMPOSITIONS | | | | |
| Base Soap (~18% moisture) | 62 | 62 | 57 | 52 |
| Sodium Carbonate | 4 | 4 | 4 | 4 |
| Alkylbenzene Sulfonate | 10 | — | — | — |
| $C_{12}$–$C_{14}$ MES | — | 2 | 2 | 2 |
| $C_{16}$–$C_{18}$ MES | — | 8 | 13 | 18 |
| Moisture/Misc. | 24 | 24 | 24 | 24 |
| FOAM INDEX: Initial/Final | | | | |
| 50 ppm hardness | 100/100 | 98/99 | 95/97 | 95/98 |
| 150 ppm hardness | 100/100 | 92/94 | 82/84 | 78/79 |
| 300 ppm hardneess | 100/100 | 486/7500 | 378/6000 | 324/5000 |

Example 4

The following example is similar to Tables 1 & 2, but includes an additional surfactant, alkyl ethoxy sulfate.

TABLE 3

| | STD | 1XB | 2XB |
|---|---|---|---|
| COMPOSITIONS | | | |
| Base Soap (~18% moisture) | 62 | 62 | 62 |
| Sodium Carbonate | 4 | 4 | 4 |
| Alkylbenzene Sulfonate | 10 | — | — |
| $C_{12}$–$C_{14}$ MES | — | 2 | 2 |
| $C_{16}$–$C_{18}$ MES | — | 8 | 8 |
| Alkyl ($C_{12-13}$) Ethoxy (3) Sulfate | — | 1 | 2 |
| Moisture/Misc | 24 | 23 | 22 |
| FOAM INDEX: Initial/Final | | | |
| 50 ppm hardness | 100/100 | 97/98 | 95/98 |
| 150 ppm hardness | 100/100 | 94/94 | 89/91 |
| 300 ppm hardness | 100/100 | 285/300 | 457/8667 |

Example 5

The following example, as shown in Table 3 illustrates the compatibility of alkyl poly glucicide in the detergent composition of the present invention.

TABLE 4

| | STD | 3XB | 4XB |
|---|---|---|---|
| COMPOSITIONS | | | |
| Base Soap (~18% moisture) | 62 | 62 | 62 |
| Sodium Carbonate | 4 | 4 | 4 |
| Alkylbenzene Sulfonate | 10 | — | — |
| $C_{12}$—$C_{14}$ MES | — | 2 | 2 |

TABLE 4-continued

| | STD | 3XB | 4XB |
|---|---|---|---|
| $C_{16}$–$C_{18}$ MES | — | 8 | 8 |
| alkyl poly glucicide | — | 1 | 2 |
| Moisture/Misc | 24 | 23 | 22 |
| FOAM INDEX: Initiai/Finai | | | |
| 50 ppm hardness | 100/100 | 98/98 | 98/100 |
| 150 ppm hardness | 100/100 | 92/93 | 94/94 |
| 300 ppm hardness | 100/100 | 159/667 | 616/9000 |

Example 6

The following example shows the compatibility of alkyl dimethyl amine oxide in the present invention.

TABLE 5

| | STD | 5XB | 6XB | 7XB |
|---|---|---|---|---|
| COMPOSITIONS | | | | |
| Base Soap (~18% moisture) | 62 | 62 | 62 | 62 |
| Sodium Carbonate | 4 | 4 | 4 | 4 |
| Alkylbenzene Sulfonate | 10 | — | — | — |
| $C_{12}$–$C_{14}$ MES | — | 2 | 2 | 2 |
| $C_{16}$–$C_{18}$ MES | — | 8 | 8 | 8 |
| Alkyl dimethyl amine oxide | — | 1 | 2 | 3 |
| Moisture/Misc | 24 | 23 | 22 | 21 |
| FOAM INDEX: Initial/Final | | | | |
| 50 ppm hardness | 100/100 | 98/100 | 100/103 | 99/100 |
| 150 ppm hardness | 100/100 | 93/96 | 95/97 | 98/98 |
| 300 ppm hardness | 100/100 | 503/7500 | 524/6500 | 876/15200 |

Example 7

The following examples are intended to show the compatibility of the following nonionic surfactants: alkyl($C_{9-11}$) ethoxylate(8), and alkyl ($C_{12-13}$) ethoxylate (6.5). However, it is noted that there is no significant enhancement of Foam Index at the hardness levels in the examples of the following Tables 6, 7 and 8.

TABLE 6

| | STD | 8XB | 9XB | 10XB |
|---|---|---|---|---|
| COMPOSITIONS | | | | |
| Base Soap (~18% moisture) | 62 | 62 | 62 | 62 |
| Sodium Carbonate | 4 | 4 | 4 | 4 |
| Alkylbenzene Sulfonate | 10 | — | — | — |
| $C_{12}$–$C_{14}$ MES | — | 2 | 2 | 2 |
| $C_{16}$–$C_{18}$ MES | — | 8 | 8 | 8 |
| Alkyl ($C_{9-11}$) Ethoxylate (8) | — | 1 | 2 | 3 |
| Moisture/Misc. | 24 | 23 | 22 | 21 |
| FOAM INDEX: Initial/Final | | | | |
| 50 ppm hardness | 100/100 | 96/96 | 95/98 | 95/97 |
| 150 ppm hardness | 100/100 | 84/84 | 91/90 | 85/93 |

| | STD | 11XB | 12XB | 13XB |
|---|---|---|---|---|
| COMPOSITIONS | | | | |
| Base Soap (~18% moisture) | 62 | 62 | 62 | 62 |
| Sodium Carbonate | 4 | 4 | 4 | 4 |
| Alkylbenzene Sulfonate | 10 | — | — | — |
| $C_{12}$—$C_{14}$ MES | — | 2 | 2 | 2 |
| $C_{16}$—$C_{18}$ MES | — | 8 | 8 | 8 |
| Alkyl ($C_{12-13}$) Ethoxylate (6.5) | — | 1 | 2 | 3 |
| Moisture/Misc | 24 | 23 | 22 | 21 |
| FOAM INDEX: Initial/Final | | | | |
| 50 ppm hardness | 100/100 | 95/98 | 97/95 | 93/94 |
| 150 ppm hardness | 100/100 | 92/93 | 88/90 | 90/89 |

What is claimed is:

1. A detergent composition comprising a surfactant mixture containing:

(a) 50% to 70% by weight base soap, (b) 1% to 6% by weight of a fatty acid methyl ester sulfonate having the formula:

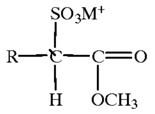

wherein R is an alkyl chain having 12 to 14 carbon atoms and M+ is a monovalent ion or a divalent ion, (c) 1% to 20% by weight of a fatty acid methyl ester sulfonate having the formula:

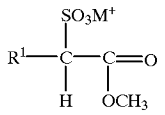

wherein $R^1$ is an alkyl chain having 16 to 18 carbon atoms and M+ is a monovalent ion or a divalent ion, to provide a hand laundry composition, said detergent composition being in the form of a solid bar.

2. The detergent composition according to claim 1 wherein the base soap contains 10–25% by weight of water.

3. The detergent composition according to claim 1 wherein the at least one fatty acid methyl ester sulfonates have a alkyl chain length of 12–18 carbon atoms.

4. The detergent composition according to claim 1 wherein M+ is a monovalent ion selected from sodium and potassium.

5. The detergent composition of claim 1 wherein M+ is a divalent ion that is capable of binding to a second fatty acid methyl ester sulfonate molecule.

6. The detergent composition according to claim 1 wherein the surfactant mixture is present in an amount of about 5–85% by weight of the detergent composition.

7. The detergent composition according to claim 1 wherein the base soap is present in an amount of about 5–95% by weight of the surfactant mixture.

8. The detergent composition according to claim 1 wherein the fatty acid methyl ester sulfonate is present in an amount of about 5–95% by weight of the surfactant mixture.

9. The detergent composition according claim 1, wherein the surfactant mixture comprises from 1% to 6% $C_{12-14}$ methyl ester sulfonate, 1% to 20% $C_{16-18}$ methyl ester sulfonate, and 50%–70% base soap based on the total weight of the composition.

10. The detergent composition according to claim 1 further comprising 0.5% to 5% of an alkyl ethoxy (0.1–4) sulfate.

11. The detergent composition according to claim 1 further comprising 0.5% to 5% of alkyl polyglucoside.

12. The detergent composition according to claim 1 further comprises 0.5% to 5% of alkyl dimethyl amine oxide.

13. The detergent composition according to claim 1 further comprising from 0.5% to 5% of an alkyl ethoxylate nonionic where the alkyl group contains from 8 to 14 carbon atoms, and the degree of ethoxylation (C—C═O)x is from 6 to 12.

14. The detergent composition according to claim 1 further comprising a sequesterant.

15. The detergent composition according to claim 1 which does not include any linear alkyl sulfonates.

16. The detergent composition according to claim 6 wherein the surfactant mixture is present in an amount of about 40–80% by weight of the composition.

17. A method for hand laundering of fabrics comprises treating a fabric with a detergent composition comprising a surfactant mixture containing effective amounts of:

(a) a base soap, and (b) at least one fatty acid methyl ester sulfonate having the formula:

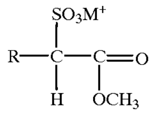

wherein R is a alkyl chain having 6 to 20 carbon atoms and M+ is a monovalent ion or a divalent ion, to provide a hand laundry composition.

18. The method according to claim 17 wherein the surfactant mixture is present in an amount of about 5–85% by weight of the detergent composition.

19. The detergent composition of claim 1, wherein said surfactant mixture consists essentially of said base soap and said fatty acid methyl ester sulfonate.

20. A detergent composition comprising a surfactant mixture containing effective amounts of:

(a) a base soap, and (b) at least one fatty acid methyl ester sulfonate having the formula:

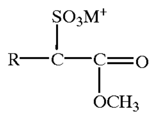

wherein R is an alkyl chain having 6 to 20 carbon atoms and M+ is a monovalent ion or a divalent ion, to provide a hand laundry composition, said detergent composition having a pH of about 10 and being in the form of a solid bar.

21. A detergent composition comprising a surfactant mixture consisting of:

(a) a base soap, and (b) at least one fatty acid methyl ester sulfonate having the formula:

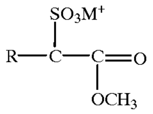

wherein R is an alkyl chain having 6 to 20 carbon atoms and M+ is a monovalent ion or a divalent ion, to provide a hand laundry composition, said detergent composition being in the form of a solid bar.

* * * * *